United States Patent [19]
Dubois et al.

[11] Patent Number: 5,045,201
[45] Date of Patent: Sep. 3, 1991

[54] GLASS MICROBEADS FOR BIOCHEMICAL SEPARATION OF MATERIAL FROM A FLUID MEDIUM

[75] Inventors: Dominique Dubois, Brussels; Marcel Deizant, Charleroi; Francois Toussaint, Montignies-le-Tilleul; Thierry Kemp, Brussels, all of Belgium

[73] Assignee: Glaverbel, Brussels, Belgium

[21] Appl. No.: 408,224

[22] Filed: Sep. 18, 1989

[30] Foreign Application Priority Data

Sep. 21, 1988 [GB] United Kingdom ............... 8822180

[51] Int. Cl.$^5$ ............................................. B01D 39/06
[52] U.S. Cl. ............................... 210/502.1; 210/504; 428/404; 428/405; 428/406; 502/407
[58] Field of Search ................. 210/502.1, 503, 504, 210/679, 690; 428/404, 405, 406; 502/407

[56] References Cited

U.S. PATENT DOCUMENTS

| | | | |
|---|---|---|---|
| 3,030,215 | 4/1962 | Veatch et al. | 428/406 |
| 4,029,583 | 6/1977 | Ho Chang et al. | 210/502.1 |
| 4,264,449 | 4/1981 | Dodd | 210/656 |
| 4,637,990 | 1/1987 | Torobin | 502/10 |
| 4,673,734 | 6/1987 | Tayot et al. | 210/502.1 |
| 4,743,545 | 5/1988 | Torobin | 435/41 |
| 4,879,247 | 11/1989 | Ohlson | 210/502.1 |

FOREIGN PATENT DOCUMENTS

| | | |
|---|---|---|
| 0059598 | 9/1982 | European Pat. Off. . |
| 127737 | 12/1984 | European Pat. Off. . |
| 0245088 | 11/1987 | European Pat. Off. . |
| 248524 | 12/1987 | European Pat. Off. . |
| 263934 | 4/1988 | European Pat. Off. . |
| 2042976 | 3/1971 | Fed. Rep. of Germany . |
| 8607281 | 12/1986 | PCT Int'l Appl. . |
| 1560788 | 2/1980 | United Kingdom . |
| 2043894 | 10/1980 | United Kingdom . |
| 2075362 | 11/1981 | United Kingdom . |

Primary Examiner—Stanley Silverman
Assistant Examiner—Krisanne Shideler
Attorney, Agent, or Firm—Spencer & Frank

[57] ABSTRACT

Glass microbeads bearing a coating which includes at least one binding agent fixed to the glass microbeads, and which binding agent is adapted releasably to bind to a material contained within a fluid medium by a biological affinity reaction, whereby the material can be removed from the fluid medium with the glass microbeads and then stripped from the glass microbeads while leaving the at least one binding agent attached to the glass microbeads. Inventive microbeads may bear a monomolecular layer of a silane as a fixing agent for a binding agent which is selected for its biological affinity for the material to be separated.

9 Claims, 5 Drawing Sheets

GLASS MICROBEADS FOR BIOCHEMICAL SEPARATION OF MATERIAL FROM A FLUID MEDIUM

BACKGROUND OF THE INVENTION

1. Field of the Invention

This invention relates to a biochemical process of separating a material from a fluid medium. The invention extends to a carrier medium for removing the material from the fluid medium and to a bioreactor and an affinity column containing such a carrier medium.

2. Description of the Related Art

The invention has particular reference to the production of various kinds of biological materials which are produced by animal or vegetable cells. Examples of such materials are viral proteins, cytokines, hormones, enzymes, monoclonal antibodies, viral and bacterial vaccines, pharmaceuticals, and cell components, such as chromosomes and cellular organelles. Other examples include whole cells, for example, for artificial skin transplants or grafts of liver, pancreatic, renal or spleen cells.

The invention is also relevant to biological materials which have been obtained by means other than biological processing, for example by mechanical crushing of biological tissue, and to materials, such as alcohols and ammonia, produced by a biological process and which need to be separated from the biological production medium. For example, certain yeasts produce alcohol which if not removed builds up to a concentration toxic to the yeast. Additionally, the invention is relevant to biochemical processes for the depollution or purification of a fluid medium.

Because of the important and increasing demand in human and veterinary medicine for biological materials which are produced by animal cells the invention will however be described hereinafter with particular reference to the production of such materials.

According to classical methods, biological materials are produced from animal cells by a fermentation process in a culture vessel from which the desired product must be separated and purified. The desired product is often highly diluted and present in only small proportions in the culture medium which also contains many contaminants. Because of the dilution, very large quantities of the culture medium need to be processed and concentrated before purification takes place. Because of the contamination, the product is very difficult to separate, and in classical methods, many separation stages are required. This is very time consuming and therefore expensive. Moreover, such processes must be performed batch-wise. Cells are grown for a period of time in a culture vessel (bioreactor) containing nutritive medium and the culture medium is then processed to remove and purify the desired product. Procedures for such purification often include separation of the cells and processing of the acellular culture medium in several purification steps which take advantage of biochemical or biophysical characteristics of the desired product in order to separate it progressively from the contaminating material. A separation step may for example be performed by passing the culture medium through a column containing a porous matrix constituted by a bed of particles such as balls of agarose or polyacrylamide which have been treated to have affinity for the desired product, and removing the product from the carrier particles e.g. by exposing the carrier particles to a medium which has a pH different from that of the culture medium. As an example, an antigen may be separated from a culture medium by coating the carrier particles with an antibody for that antigen. Since such multistep and batch-wise processing requires storage of the biological medium to be purified, exposing it to the risk of degradation, and requires adaptation of the individual reactants at each successive step, it is by its very nature inefficient and expensive.

SUMMARY OF THE INVENTION

It is an object of the present invention to provide a biochemical process of separating a material from a fluid medium in which at least some of these disadvantages are reduced.

According to this invention, there is provided a biochemical process of separating a material from a fluid medium comprising introducing into the fluid medium a plurality of glass microbeads to whose surfaces is fixed a binding agent for said material, allowing the microbeads to remain in the fluid medium for a sufficient dwell time for a quantity of said material to bind to the microbeads, removing from the fluid medium microbeads with bound material, stripping at least some of the bound material from the microbeads while leaving binding agent fixed to the microbeads and recycling with binding agent to the fluid medium.

The invention includes processes in which the product collected after stripping from the microbeads is not identical with the material which is separated from the fluid medium. For example the molecules of that separated material may be altered while bound to the microbeads or during stripping from those microbeads.

By the present invention, there is provided a biochemical process in which a carrier medium comprising glass microbeads bearing a binding agent is cycled through the fluid medium so that removal of the material from that medium may be effected in a single step or continuously, and this is inherently more efficient and therefore less costly than multi-step batch-wise removal techniques such as have hitherto been used. Also, because microbeads with binding agent are recycled to the fluid medium, the binding agent is itself reusable for separation of the material. The quantity of the binding agent required for removing a given quantity of material is therefore very much reduced, and accordingly so is the cost of providing that binding agent.

The invention includes glass microbeads which may be used in such a process.

The invention accordingly also provides glass microbeads bearing a coating, characterised in that said coating comprises at least one binding agent fixed to the microbeads and adapted to bind releasably to a material within a fluid medium by biological affinity reaction, whereby the material can be removed from the fluid medium bound to the microbeads and then stripped from the microbeads while leaving binding agent attached to those microbeads. By simultaneously employing more than one binding agent, whether on a same or a differently-treated carrier, it is possible to effect the simultaneous removal of different materials from the fluid medium.

Such microbeads are useful in processes for separating biological materials, and they are economical in that they are re-usable. It will be appreciated that the major cost of such microbeads lies not in the cost of the glass, but rather in the cost of the binding agent itself and in the cost of the process of fixing the binding agent to the microbeads. Because they are re-usable, such costs can be apportioned over a longer useful life.

The use of glass microbeads gives important advantages. Glass microbeads can be made easily and inexpensively, and it is quite easy to apply a suitable technique in order to fix the binding agent to the surfaces of such beads. Glass microbeads are easily sterilizable and easily handled, and they may be given properties which render their use as carrier particularly suitable. In constrast to other types of beads, glass beads do not tend to swell upon prolonged exposure to a fluid medium or when the ionic concentration within that medium varies, and thus they ensure more reliable and consistent hydrodynamic qualities during the separation, whether during the collection of the material, for example from a bioreactor, or during stripping of the material from the binding agent, for example in an affinity column.

Advantageously, said microbeads are least mainly constituted by glass microspheres having non-porous surfaces. This is a particularly desirable property because beads having non-porous surfaces do not have pores which could adsorb and trap contaminants or other undesired materials, for example from the fluid medium or a medium used for stripping the material from them. Indeed the fluid medium supporting cell growth contains not only cells and the desired product, but also many soluble contaminants and cellular debris, such as pieces of cellular membranes, and aggregates and organelles of cellular origin. Such contaminants are able to be adsorbed or entrapped in pores to spoil the purity of the desired product and could poison or have some other deleterious effect on the cells if porous beads were to be recycled to the fluid medium. It can be extremely difficult to remove trapped material from pores of glass microbeads, or indeed from pores of beads of any other material. Non-porous beads, however, may be re-used easily without any special treatment: they simply be intensively washed before and after stripping of the purified product without having any deleterious effect on the binding agent or desired product.

The glass microbeads are preferably of a density related to the density of the medium and to the intended procedures of addition to, contact with and removal from the medium. In general it is preferred that they have an average relative density between 0.5 and 1.5. They may be solid microbeads, which will have a density greater than the fluid medium, which may be introduced into the top of a vessel containing the fluid medium and removed from close to its base. Alternatively and preferably they are at least mainly constituted by hollow glass microspheres. These may have a density considerably less than the fluid medium, in which case it would be appropriate to introduce them at the base of the a vessel and remove them by skimming the surface of the fluid medium. Such low density beads are particularly suitable for use with a medium which must be agitated. In many preferred embodiments of the invention, said microbeads have an average relative density between 0.9 and 1.1. Such beads are easily suspended in many of the fluid media in view, have a substantially neutral or slight positive buoyancy within the medium and may readily be circulated with the medium through a system of pipework. This is advantageous for achieving a good mixing of the beads within such media and for allowing a suitable dwell time for the effective collection of the product.

The size of the microbeads also has a bearing on their effectiveness as a carrier medium for the binding agent. Processing of the beads is facilitated if, as is preferred, they have a median diameter below 125 μm, for example 75+15 μm. That is to say, it is preferred if most of the beads (by number) have a diameter less than 125 μm. It is also desirable that the beads should have a rather narrow size range spread. For example it is preferred that their upper decile diameter (than which 10% by number have a greater diameter) is no more than twice their lower decile diameter (than which 10% by number have a lesser diameter). Alternatively, or in addition, it is sometimes desirable that their upper and lower decile diameters should differ by less than 20 μm. Such a narrow size range spread of the beads, which is more easily achieved with glass than with other bead-forming substances, is found in particular to facilitate filtration of the beads and the elution of material therefrom. It is particularly preferred that the microbeads should have a median diameter in the range 20 μm to 30 μm. This gives the beads a high specific surface area which is especially suitable for the fixing thereto of the binding agent and for binding the material to be separated to such binding agent.

It is preferred that the binding agent is fixed to the glass surfaces of the beads by means of a fixing agent. This facilitates a strong fixing of the binding agent to the beads to resist removal of that binding agent during processing of the beads to remove bound material, and, advantageously, said binding agent is fixed to the glass surfaces of the beads by covalent bonding.

The fixing agent is typically a rather long chain molecule which attaches itself firmly to the glass at one end of the chain and to the binding agent at the other end of the chain. The attachment to the binding agent must be such that it does not hinder the capability of the binding agent to affix itself to the material to be separated from the fluid medium.

Various fixing agents which are capable of binding to glass and to organic materials are known per se and may be used in this invention. It is preferred that said fixing agent comprises a silane, most preferably silanes containing 6 to 18 carbon atoms in the molecule. A wide range of silanes is available commercially, and an appropriate silane which bonds well to glass and to the particular binding agent in view may be selected. A particularly suitable silane is an amino-silane or an epoxy-silane, for example gamma-glycidoxypropyltrimethoxysilane. The fixing agent may be formed in situ, for example, amino-alkyl-silane together with glutaraldehyde. The methoxy functions of gamma-glycidoxypropyltrimethoxysilane fix strongly to glass, while the epoxide function is particularly suitable for forming covalent bonds mainly with amino groups of proteins within which class fall the most favoured binding agents. In an alternative embodiment the silane can be attached to a sugar which forms part of a glycoprotein, glycolipid, or polysaccharide serving as binding agent. Such reaction with sugar is normally effected after the sugar has been treated with an oxidising agent which reacts with the sugar to create active sites at which the attachments can occur.

In preferred embodiments of the invention, said fixing agent is applied to said microbeads substantially as a monomolecular layer. This promotes the formation of a strong bond between the glass and the binding agent. Such layer preferably extends over substantially the whole surface of the microbeads for fixing the maximum amount of binding agent. In this way, a molecule of binding agent links directly to a molecule of fixing agent which in turn links directly to the glass. A monomolecular layer is less susceptible to damage, for example by abrasion, and this greatly reduces the risk that fixing agent and fixed binding agent may be stripped off to contaminate the material which it is desired to separate. Furthermore, the adoption of this feature leaves fewer sites on the coated beads which are capable of attaching to materials other than the desired material. The adoption of this feature is also economical of fixing agent and binding agent. Moreover, the use of a monomolecular layer of fixing agent is beneficial for avoiding that units of binding agent will be fixed to the carrier at more than one location, thus respecting the molecular movement of biological macromolecules and promoting maximum site-availability for binding of the material to be separated from the fluid medium.

The invention is particularly suitable for the separation of biological materials produced by animal cells, for example viral proteins, cytokines, hormones, enzymes, monoclonal antibodies, viral and bacterial vaccines, pharmaceuticals, whole cells, and cell components such as chromosomes, and cellular organelles.

The invention gives particular advantages of simplicity of operation and of economy when said fluid medium is a culture medium and said material is a product of that culture medium.

The invention is especially useful for separating an antigen from a culture medium, and for this purpose it is especially preferred that said binding agent and said material function as an antigen-antibody pair, with the antibody as the binding agent attached to the beads. The adoption of this preferred feature of the invention greatly facilitates the separation and purification of the desired material due to the highly selective affinity between such a material and such a binding agent. For example an immunoglobulin of the type IgG or IgM (pentamer) may be used. Other binding agents may be used, for example protein A or protein G, which also have affinity for several animal antigens. Alternatively, for separating an antibody from the fluid medium, its corresponding antigen or haptene or a molecule representing the antigen site, may be used as the binding agent which is fixed to the beads. The antigen may be part of a particle such as a whole cell or a cellular fraction.

In addition, the invention is useful in the transformation of molecules of a biological or organic material to be separated from the fluid medium. Such molecular transformation is of particular interest when the material in its original form in the fluid medium is environmentally harmful, when the transformed material is a more useful form of the material originally in the fluid medium, or when the reaction between the material and the binding agent is useful as an indicator for the presence of that material in the fluid medium.

The microbeads may be cycled through the fluid medium in various ways. For example, buoyant microbeads may be allowed to remain in the medium (which is preferably agitated) for a desired dwell time and then skimmed off from the surface. Alternatively, using a tall vessel for containing such a medium, such microbeads may be introduced at its base and collected from the surface of the medium.

In the embodiments of the invention in which the microbeads are cycled through a culture vessel, significant advantages are given by the use of rotating filter elements (spin filters) which confine the microbeads to a space defined by the filter elements within the culture vessel and allow passage of the material into that space while substantially excluding from it culture cells of the medium.

Microbeads carrying said material are preferably passed to an affinity chromatographic column for the stripping of the material therefrom. This is a simple and convenient way of processing batches of microbeads carrying material. A plurality of such columns may be associated with a single culture vessel as desired to allow sufficient time for stripping of material in any given column while maintaining a sufficient reserve of the microbeads for recycling to the culture vessel. The material may for example be stripped from the microbeads by elution with an acidic medium. A particular advantage of the invention is that such removal of the material can be effected in a continuous manner.

Contamination of the system may be avoided by preparing sterile microbeads using sterile equipment and sterile handling techniques, and further contamination may be controlled as desired by the use of a suitable antibiotic preparation. For example a fluoroquinolone may be used.

The invention extends to a bioreactor in which glass microbeads according to the invention are used.

Accordingly, this invention extends to a bioreactor comprising a vessel containing a fluid medium and microbeads as herein defined, and wherein means is provided for continuously removing and for continuously introducing said microbeads from and into said medium. Specifically the invention provides a bioreactor for containing a fluid medium, characterised in that said reactor includes a first zone for contacting the fluid medium with glass microbeads which carry a binding agent for a component of the fluid medium and a second zone for subsequent separation of the said component from the microbeads.

There are a variety of ways in which the two zones may be provided in the reactor: the zones may be in separate but interconnected vessels or they may be in different compartments within a single vessel. One convenient means of providing different zones within the same vessel is to employ perforated sheets or sieves, for example of stainless steel mesh, between them. Mesh formed into a cylindrical shape is especially convenient for this purpose. The cylinder is preferably also provided with means to rotate it so as to prevent passage of certain components of the fluid medium through the mesh and so as to reduce the risk of clogging. Such rotating mesh cylinders are referred to herein as spin filters. They can also be of a type which can be lowered and raised into and out of the fluid medium, thereby allowing the beads to pick up the desired component from within the fluid medium, to be removed with the cylinder from the fluid medium and be separated from the desired component while still retained within the cylinder.

A particularly preferred version of bioreactor with spin filters comprises a vessel for containing a fluid medium and inner and outer filters which define an annular space between them within said vessel, means for driving said filters in rotation substantially to exclude suspended material of said medium from said annular space while allowing a soluble product of a biological process dissolved in such medium to enter that space, and means for circulating glass microbeads through said annular space.

The use of such a very simple construction of bioreactor gives an efficient and economical biochemical process for the separation of a material from a culture medium. The use of two such rotatable filter elements (referred to herein as a double spin filter) gives significant advantages. The microbeads can be confined to a well defined area of the culture vessel so that cycling the beads through that space while allowing a desired dwell time therein is simplified. This promotes efficiency of the separation process. Because the culture cells of the medium can be excluded from the region of the microbeads, binding of the material to the binding agent may proceed unimpeded. A further advantage of using a double spin filter is that the maximum size of the particles which a given filter element will pass can be varied, down from the size of the apertures in the filter element, by increasing the rate of spin of the filter. Accordingly, a single double spin filter may be used, at different times, in the processing of different materials which would otherwise require two differently sized double spin filters. Yet a further advantage is that the apertures in rapidly rotating spin filter elements are very much less likely to become clogged than are those of stationary filter elements. The process can for example proceed by perfusion from an entry compartment to an exit compartment separated or defined by such spin filters.

Means may be provided for drawing fluid from a space within the inner of said filters and for conveying that fluid for contact with microbeads externally of the vessel, and subsequently returning that fluid to the vessel. This is a very simple way of providing fluid for example for transporting or rinsing the microbeads while making efficient use of the fluid medium and maintaining a sufficient quantity thereof in the culture vessel.

In preferred embodiments of the invention, at least one affinity column is provided associated with means for conveying microbeads to that column and for returning microbeads to the vessel.

The invention extends to an affinity column containing coated microbeads as herein defined. Such a column has good hydro-dynamic properties when packed, and it can easily be voided by flushing with a fluid medium, for example a culture medium which allows the column and microbeads to remain in a sterile circuit.

BRIEF DESCRIPTION OF THE DRAWING

Several preferred embodiments of the invention will now be described by way of example with reference to the accompanying figures, in which.

DESCRIPTION OF THE PREFERRED EMBODIMENTS

Figure 1:
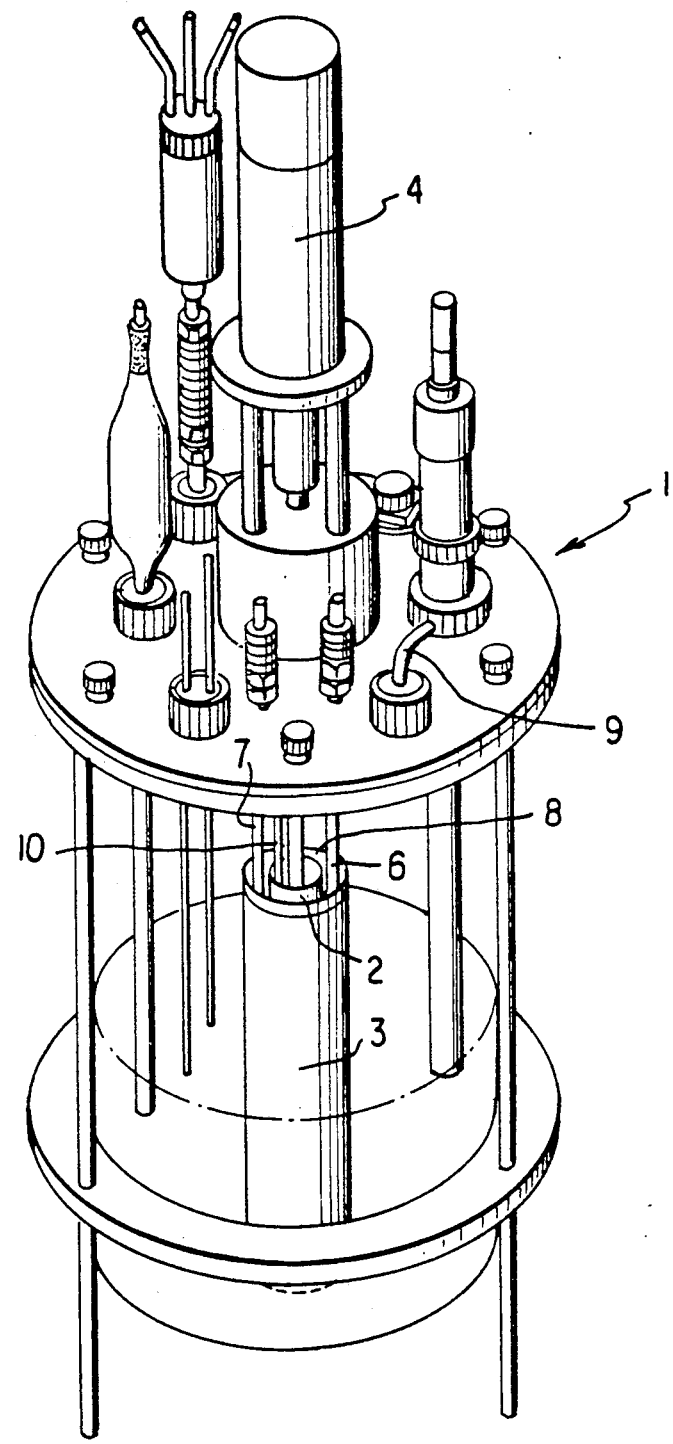
FIG. 1 is a diagrammatic perspective view of a bioreactor in which part of the casing has been cut away to reveal the internal details.

The drawing of a bioreactor in FIG. 1 shows a culture vessel 1 which holds a pair of coaxial cylindrical filter elements 2, 3 with a common base and together forming a double spin filter. The filter elements 2, 3 are suitably of stainless steel mesh with openings of 5 $\mu$ to 10 $\mu$m. They are driven in rotation by a motor 4, for example at a speed of 100 rpm. The system for stirring the fluid culture medium is not shown. The stirring of the culture medium may be independent of the rotating double spin filter used. Conduits 6 and 7 are provided for circulating glass microbeads bearing binding agent through the annular space 8 between the two elements 2, 3 of the double spin filter. Conduit 9 is for the supply of culture medium to the culture vessel externally of the double spin filter, and conduit 10 is for the extraction of fluid from the central space of the double spin filter. Means (not illustrated) is also provided for monitoring and regulating the pressure within the culture vessel 1, the liquid level, dissolved carbon dioxide and oxygen, temperature and pH within the culture medium, the speed of rotation of the double spin filter and the circulation of the microbeads.

In a typical example employing the bioreactor shown in FIG. 1, hollow glass microbeads having an average relative density of just below 1.0 are graded to give a batch having diameters between 20 $\mu$m and 30 $\mu$m. The beads are first washed in hydrochloric acid and, if desired, in a detergent. Specifically, a batch of 20 g of beads is first washed in hydrochloric acid for a period of one hour at a temperature between 20° C. and 80° C. This treatment has an important effect on the ionic equilibrium of the glass and on its stability when exposed to a biologically active environment. The acid-washing treatment can destroy beads having walls which are too thin or not fully formed. The beads are decanted to separate well-formed beads from the debris of mal-formed beads which latter tends to sink, and they are then flushed with demineralised water until the pH of the eluent returns to between 6 and 7, and the beads are then dried to constant weight at a temperature of 130° C.

In a variant, the microbeads are selected to have an average relative density of 0.51 and diameters between 53 $\mu$m and 90 $\mu$m.

A fixing agent is then attached to the surfaces of the treated microbeads. The fixing agent chosen in this example is gamma-glycidoxypropyltrimethoxysilane. In a first method, 2 ml of silane is dissolved in 75 ml of toluene for the treatment of 15 g of beads. The beads are immersed in the solution for 18 hours at 110° C., then removed and successively washed in 200 ml toluene, 100 ml methanol, and then in demineralised water. In a variant, the fixing agent used is N-trimethoxysilylethylenediamine.

In a second method, 1.2 ml of silane is dissolved in 60 ml of an aqueous solution of 0.1 mol sodium acetate buffered to a pH of 5.5, and 15 g of microbeads are treated in that solution for 4 hours at 90° C. and then washed with demineralised water. In this treatment, some of the epoxide functional groups are hydrolysed into diols. In order to complete hydrolysis, the beads are treated with an aqueous solution of sulphuric acid at pH 3 for two hours in an amount of 40 ml solution per gram of beads. The beads are then washed in distilled water.

In order to promote the ability of the silane to fix proteinaceous material to the microbeads, the diol groups are in turn reacted with periodate ions to form aldehyde groups. 5 g of such beads are suspended in 50 ml methanol cooled by ice, and a solution of 380 mg NaBH$_4$ and 30 mg NaOH in 10 ml water is added in 2 ml portions. Temperature is allowed to come to ambient, and the suspension is then heated to 40° C. during 15 minutes. The beads are then successively washed in water, acetone and ether and then dried under vacuum at 70° C. for 2 hours. This converts the diol groups to primary alcohol groups. Under these condition, testing with 2,4-dinitrophenylhydrazine is negative, indicating the absence of residual carbonyl functional groups as the microbeads remain white.

3 g of the thus treated microbeads are then treated with 70 mg of 1,1'-carbodiimidazole (an excess of about 100-fold) in 25 ml anhydrous dioxane. After 2 hours at ambient temperature, the microbeads are filtered off, washed in ether and dried in a desiccator under vacuum. This leaves the glass microbeads coated with a silane having an imidazoyl carbamate functional group which is well able to fix any $H_2N$-protein.

Microbeads bearing fixing agent attached as described were tested for their ability to fix proteins using bovine serum albumin (BSA). 250 mg beads were used in each test. The beads were agitated by horizontal rotation at 60 rpm in 1.5 ml of a solution buffered with 100 mM borate and 150 mM NaCl to pH 9.0 containing 5 mg BSA per ml at a temperature of 20° C. The beads whose fixing agent comprised epoxide functional groups fixed an average of 80 μg BSA after 2 hours treatment. The beads whose fixing agent comprised imidazoyl carbamate functional groups fixed an average of 424 μg BSA after 2 hours treatment, and an average of 480 μg BSA after 4 hours treatment.

The choice of binding agent depends of course on the product it is desired to collect and purify. In the following example it is assumed that the product to be collected and purified is a mouse monoclonal antibody $IgG_1$ produced by mouse hybridomas growing in the bioreactor.

As binding agent for fixing to the fixing agent was chosen total serum of rabbit immunised against mouse immunoglobulin $IgG_1$ (RAM [rabbit-anti-mouse]-serum). The $IgG_1$ is recognised as foreign antigen by the rabbit and gives rise to the in vivo production of rabbit immunoglobulin antibody specifically directed against the antigen.

Glass microbeads bearing fixing agent are treated at a rate of 250 mg per ml of treatment solution. The treatment solution was borate buffered and contained 20 mg/ml RAM serum. The beads were suspended in the treatment solution for 2 hours at 20° C. while agitated by horizontal rotation at 60 rpm, whereafter a post-reaction incubation of 16 hours at 7° C. took place. It was found that the microbeads covalently fixed 660 μg of RAM serum per gram of dried beads, when measured by a Folin-Lowry method modified for supported proteins.

After fixing of the binding agent, it is desirable to inactivate any remaining sites of unused fixing agent in order to promote the specificity of the microbeads in binding a desired material. This is done by washing the microbeads with fixed binding agent in a buffer solution of containing 150 mM glycine-NaOH at a pH of 9, and then washing the beads in a neutral buffer.

Such a polyclonal serum binding agent may if desired be replaced by a monoclonal antibody. Such a monoclonal antibody can be obtained from a culture of hybridomas or transformed lymphocytes, for example rat hybridomas producing rat monoclonal antibodies (IgR), in order to recognise a single antigenic characteristic of a mouse immunoglobulin, and can be fixed in the same way.

Mouse immunoglobulin $IgG_1$ to be purified is produced by mouse hybridomas in a suitable medium in the culture vessel. A suitable culture medium is formed by Dulbecco Modified Eagle's Medium containing serum, or serum substitute. The pH is adjusted to 7.2. The culture medium additionally contains an inhibitor (e.g. pepstatine A or phenyl methyl sulphonyl fluoride) to prevent production of enzymes which would otherwise digest the proteins present. The culture medium is introduced into the culture vessel to surround the double spin filter. The filter is controlled to allow passage of the culture liquid and any dissolved material but to keep the culture cells to that surrounding region of the culture vessel.

Using the apparatus illustrated in FIG. 1, the beads bearing binding agent are introduced into the space 8 between the filter elements so that they are immersed in the culture liquid which contains dissolved $IgG_1$. The beads bearing bound product are continuously removed from the culture medium through conduit 7 in culture liquid as carrier and passed to a chromatographic column (not shown), in which they constitute the chromatographic matrix. The culture carrier liquid may be returned to the culture vessel via conduit 9. The $IgG_1$ product is stripped from the microbeads by elution using, for example, an acidic medium and low-to-moderate pressure, whereafter microbeads still having fixed binding agent are recycled to the culture vessel using as carrier fluid culture liquid withdrawn from the centre of the double spin filter via conduit 10. The required $IgG_1$ product is immediately buffered to prevent denaturation, its identity verified by enzyme linked immunosorbent assay, and its purity checked by electrophoresis.

In a variant, the conduit 7 itself is constituted as a chromatographic column through which culture fluid is continuously circulated so that binding of the $IgG_1$ product proceeds continuously. The column is withdrawn after a suitable dwell time and is replaced after elution of the product. In such a column having a bead content of 20 g and a capacity of 2 mg of mouse $IgG_1$, a factor of purification of 750 times was achieved in a single step with protein electrophoresis showing a pure product.

Stringent precautions are taken to maintain sterile conditions and to exclude contaminants from the culture vessel, and culture liquid and microbeads still bearing binding agent are recycled thereto to maintain desired levels. A broad spectrum antibiotic which does not poison or contaminate the cells, such as a fluoroquinolone, may be used.

In a variant which yields similar results, microbeads are treated with amino-silane and glutaraldehyde as fixing agent.

In another variant, the microbeads are coated with an amino-silane as fixing agent. The oligosaccharide chains of an immunoglobulin such as that called IgR in this Example which is to serve as antibody binding agent are oxidised. For this purpose, 1 mg of IgR is used per gram of beads. 20 μl of a solution (0.5M) of $NaIO_4$ are added per ml of a solution containing the IgR in an acetate medium with pH 5.5. Oxidation is allowed to proceed for 20 minutes at ambient temperature with intermittent agitation. The oxidised IgR is then separated from the oxidation medium by a classical chromatographic technique. Oxidised IgR in solution is then added to the silanised microbeads in an amount of 2 ml solution to 1 g beads in a reaction vessel rotating at a rate of 30 to 60 rpm. After 24 hours, the beads are treated for 2 hours, still at ambient temperature and under slow rotation, with a solution of glycine to deactivate any remaining free sites on the glass. The microbeads are then washed on a Buchner filter, and placed in contact with a phosphate buffer solution (2 ml per gram of beads). 20 $\mu$l of reducing solution of $BaBH_3CN$ (0.5M) is added per ml of buffer solution, and left for 4 hours with slow rotation at ambient temperature before washing again on a Buchner filter. The microbeads are recovered and stored cold in a buffer solution (0.01M, pH 7.4) of 3-(N-morpholino)propane sulphonic acid (MOPS) containing NaCl and $NaN_3$ until required for use.

Figure 2:
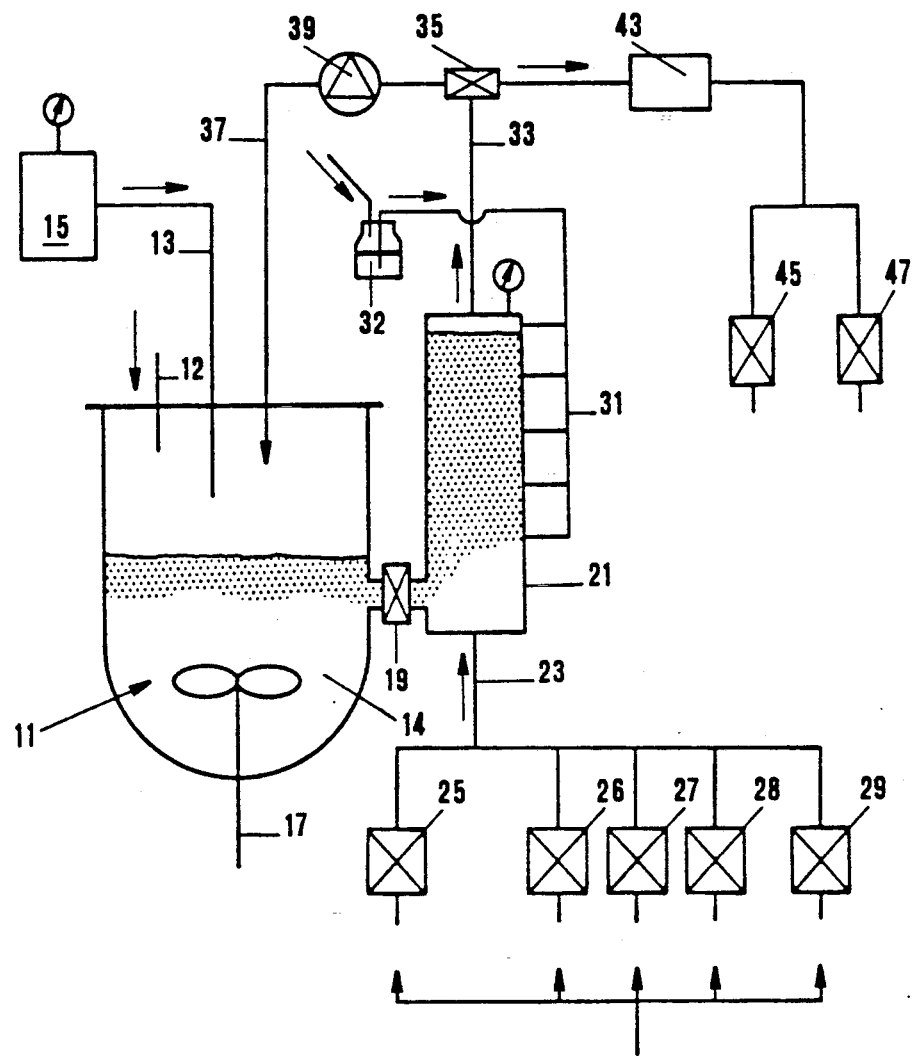
FIG. 2 is a flow diagram of a second version of bioreactor system.

The bioreactor system illustrated in FIG. 2 comprises a culture vessel 11 to which binder-coated glass beads are supplied through conduit 13 from hopper 15. The vessel 11 also contains the biological fluid culture medium from which the desired material is to be separated. An agitator 17 is provided to assist mixing of the beads in the fluid medium. A valved outlet line 19 connects the vessel 11 to a chromatographic column 21. A feed conduit 23 supplied with a five different fluid supply lines, 25, 26, 27, 28 and 29, each fitted with a control valve, leads to the base of the column 21. The fluids to be supplied in turn through the lines 25, 26, 27, 28 and 29 are, respectively, column washing fluid (MOPS buffer solution), first column cleaning fluid (high ionic strength solution), second column cleaning fluid (ammonium acetate solution), material eluting fluid (glycine-HCl buffer solution) and, as, bead rinsing fluid, N-(2-hydroxyethyl)-piperazine-N'-3-propane sulphonic acid (HEPPS) buffer solution containing NaOH. A pipeline manifold 31 leads to the side of the column 21 from a fluid reservoir 32 and serves to introduce fluid at different levels into the column 21 to assist in separating beads from the column for their return to vessel 11. The main outlet from the column 21 is a conduit 33 leading to a valve 35 which can direct fluid from the column 21 via a line 41 through a spectrophotometer 43 to a choice of valved waste line 45 or valved product line 47. The valve 35 can alternatively direct fluid and/or beads via a line 37 fitted with a pump 39 leading back to the vessel 11.

The FIG. 2 system requires the beads to be of relatively low density, for example 0.5 to 0.9, so that they can float upwards through the vessel 11 and column 21.

In operation of the FIG. 2 bioreactor system the binder-coated beads are fed into the vessel 11 through line 13 where they are thoroughly mixed with the biological fluid under the action of the agitator 17. After a sufficient dwell time, the agitation is stopped, the valve 19 opened and the beads, now carrying the material separated from the medium in vessel 11, float upwards through the column 21. After washing and cleaning the beads through the lines 25, 26, and 27, the desired product is separated from the beads by an eluting fluid from line 28. The eluate is fed to the line 33 and valve 35 where the spectrophotometer 43 monitors the presence of proteins in the eluate and opens valve 47 to collect the product, the washing and cleaning solutions having been up to that point discarded to waste through valve 45. When all the required product has been removed the beads in column 21 are subjected to a rinse and wash cycle (lines 29 and 25). The matrix is dismantled by injection of culture medium from reservoir 32 under moderate pressure and the beads are then recycled through valve 19 to the vessel 11, ready to bind new biological material to be separated, the latter being continuously produced in the bioreactor.

Figure 3:
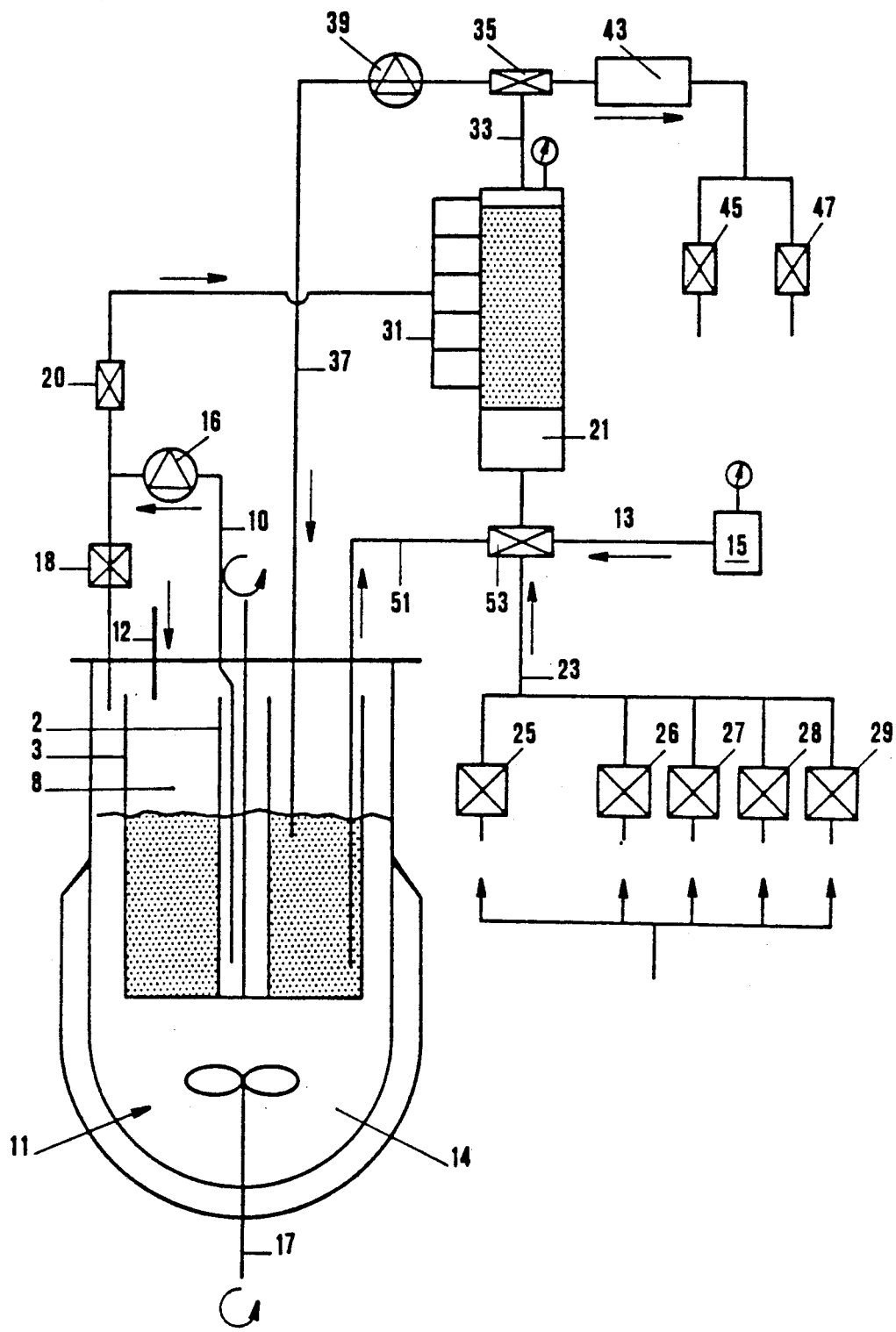
FIG. 3 is a flow diagram of a third version of bioreactor system.

The bioreactor system shown in FIG. 3 has many features similar to those of the FIG. 2 system and these are shown by equivalent reference numerals. In the FIG. 3 system however the vessel 11 includes a double spin filter formed by filter elements 2, 3 similar to those of FIG. 1. For sterile introduction of microbeads into the purification system, the bead supply line 13 in the FIG. 3 system leads through a switching valve 53 to the bioreactor. A conduit 51 leads from the annular space 8 to the valve 53 so as to convey beads carrying separated material from the vessel 11 to the column 21 while recycling the bead-free fluid to the reactor via valve 35 and pump 39. A conduit 10, fitted with a pump 16, leads from the inner chamber formed by the filter element 2 of the spin filter 2, 3, and to a valved line 20 which leads to the manifold 31.

In operation of the FIG. 3 bioreactor system, the binder-coated beads carrying separated material pass through line 51 and valve 53 to the column 21. In this system the beads are required to have a density of about 1.0. The desired product material is separated from the beads by an eluting fluid from line 28. The wash/clean-/elute/rinse manifold 25, 26, 27, 28, 29 and its operation are generally similar to that of FIG. 2. The eluate is similarly fed to the line 33 where the spectrophotometer 43 monitors the presence of protein and opens valve 47 when required. After washing and rinsing the matrix is dismantled by injection of culture medium taken from within the inner spin filter under the action of pump 16 and valve 20. Beads are returned from column 21 to the annular space 8 via valve 53 and line 51.

Figure 4A:
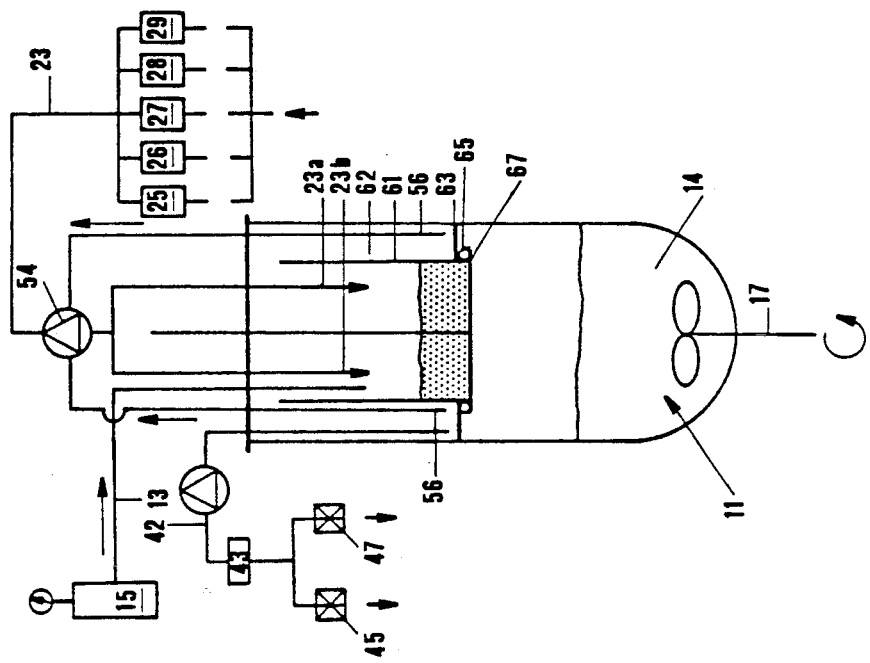
FIGS. 4a and 4b are flow diagrams of a fourth version of bioreactor system.
Figure 4B:
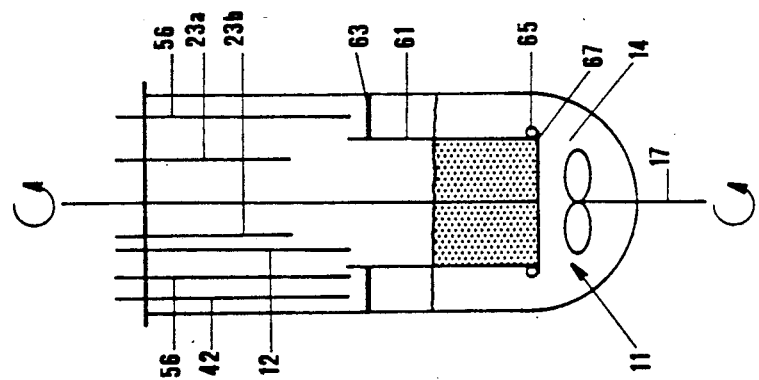

The bioreactor system shown in FIGS. 4a and 4b differs from the other illustrated systems in having a single spin filter 61 and no chromatographic column. In this system the spin filter is adjustable in height between an upper position (shown in FIG. 4a) and a lower position (shown in FIG. 4b). An annular baffle plate 63 defines the upper limit of movement of the spin filter 61. A flange 67 on the base of the spin filter 61 carries an annular seal 65 which comes into sealing abutment with the plate 63 at the upper limit of travel of the spin filter 61. The conduit 23 from the wash/clean/elute/rinse manifold 25, 26, 27, 28, 29 leads via a switching valve 54 to a forked supply line 23a/23b and thence to the interior of the spin filter 61. Lines 56 also lead to valve 54 from the annular space 62 formed, when the spin filter 61 is in its upper position, between the spin filter 61 and the walls of the vessel 11. A product extraction line 42 leads from the annular space 62 to the product separation unit 43, 45, 47.

In operation of the FIG. 4a/b bioreactor system the spin filter 61 containing binder-coated beads having a relative density of about 1 is lowered into the fluid 14 (FIG. 4b) and remains therein for a period sufficient to effect binding of the desired product material to the coated beads. The spin filter 61 is then raised to the upper position (FIG. 4a) and the product material is separated from the beads following a wash/clean-/elute/rinse cycle similar to that of FIG. 2.

Figure 5:
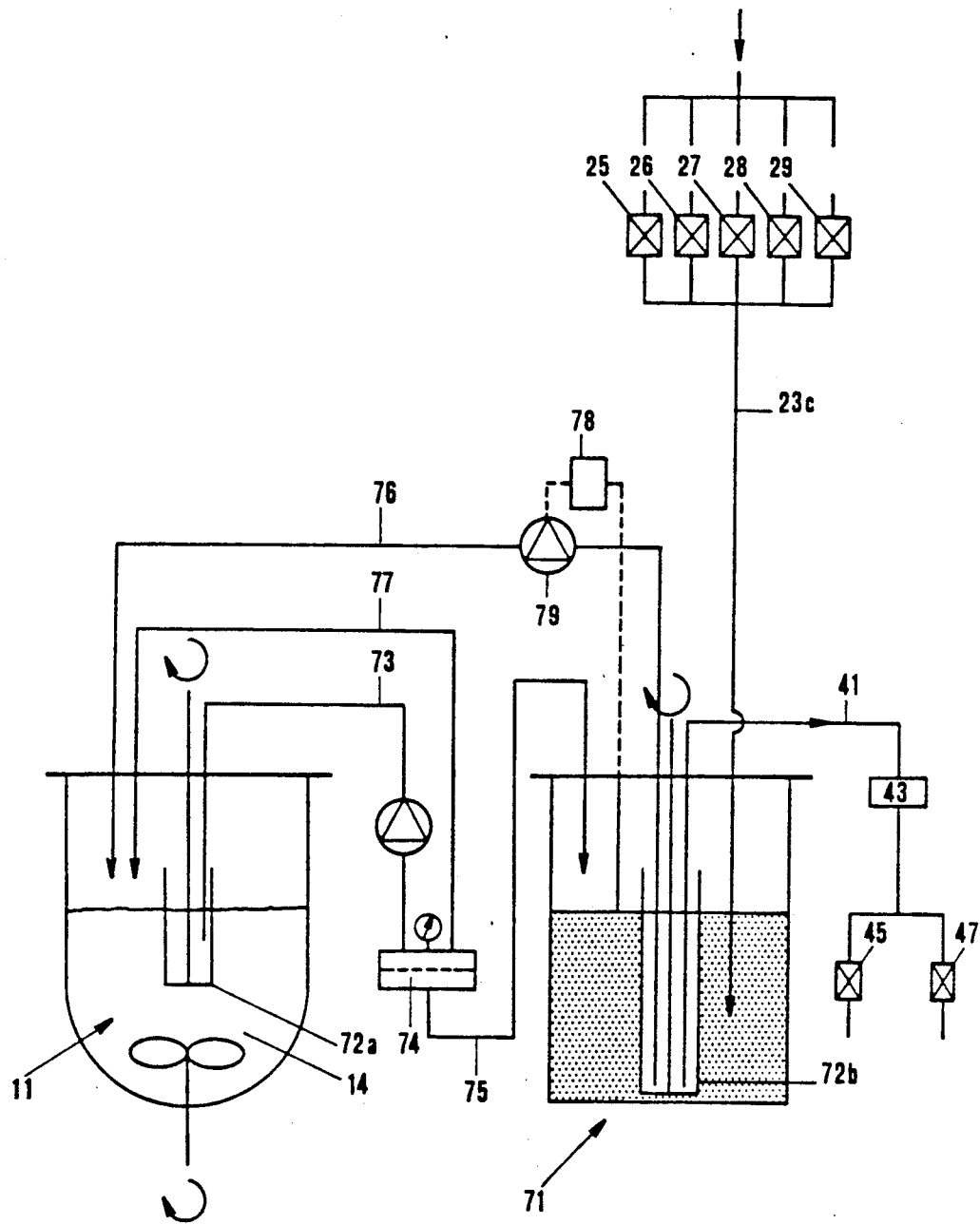
FIG. 5 is a flow diagram of a fifth version of bioreactor system.

The bioreactor system shown in FIG. 5 incorporates two vessels 11 and 71, each having spin filters (respectively 72a and 72b). In this version the culture medium 14 is filtered at 72a in vessel 11 and then conveyed via line 73 to membrane filter 74, to retain any cell debris which might have passed the spin filter 72a, and then via line 75 to the vessel 71, in which binder-coated beads remove the desired product material. The beads, which have a relative density of about 1, remain throughout in vessel 71. Lines 76 and 77 permit recycling of the residual fluid to the vessel 11, line 76 being activated by a control device 78 which monitors the fluid level in vessel 71 and activates a pump 79 when the level in vessel 71 rises above a set limit. After a sufficient period of time, fluid recycling is halted and the wash/clean/elute/rinse fluids are fed to the vessel 71 through a supply line 23c and separated product is removed through line 41 in a similar manner to the other versions.

What is claimed is:

1. Glass microbeads, comprising:
   glass microbeads which are glass microspheres having non-porous surfaces and which bear a coating comprised of at least one binding agent and at least one fixing agent which fixes the at least one binding agent to the non-porous surfaces of the glass microspheres by covalent bonding, and which at least one binding agent is capable of releasably binding, by a biological affinity reaction, a material contained within a fluid medium when in contact therewith, whereby the material can be removed from the fluid medium with the glass microbeads and then stripped from the glass microbeads while leaving the at least one binding agent attached to the glass microbeads.

2. The glass microbeads according to claim 1, wherein said glass microbeads are hollow glass microspheres.

3. The glass microbeads according to claim 2, wherein said glass microbeads have an average density ranging between 0.5 and 1.5 relative to the fluid medium.

4. The glass microbeads according to claim 3, wherein said glass microbeads have an average density ranging between 0.9 and 1.1 relative to the fluid medium.

5. The glass microbeads according to claim 1, wherein said glass microbeads have a median diameter below 125 $\mu$m.

6. The glass microbeads according to claim 5, wherein at least 90% of said glass microbeads have a diameter ranging between 20 $\mu$m and 30 $\mu$m.

7. The glass microbeads according to claim 1, wherein said fixing agent comprises a silane.

8. The glass microbeads according to claim 1, wherein said fixing agent is applied to said glass microbeads substantially as a monomolecular layer.

9. The glass microbeads according to claim 1, wherein said at least one binding agent is one of an antigen or an antibody.

* * * * *